US007847276B2

(12) United States Patent
Carlisle et al.

(10) Patent No.: US 7,847,276 B2
(45) Date of Patent: Dec. 7, 2010

(54) IMPULSE ANALYSIS FOR FLOW SENSOR-BASED FLUID CONTROL SYSTEM

(75) Inventors: Jeffrey A. Carlisle, Stratham, NH (US); Charles E. Kramer, Cave Junction, OR (US); John M. Kirkman, Jr., Trumansburg, NY (US); Douglas E. Vincent, Pelham, NH (US)

(73) Assignee: Fluidnet Corporation, Amesbury, MA (US)

( * ) Notice: Subject to any disclaimer, the term of this patent is extended or adjusted under 35 U.S.C. 154(b) by 349 days.

(21) Appl. No.: 12/048,612

(22) Filed: Mar. 14, 2008

(65) Prior Publication Data

US 2009/0234594 A1 Sep. 17, 2009

(51) Int. Cl.
*G01F 1/00* (2006.01)
*G01N 15/00* (2006.01)
(52) U.S. Cl. .................. 250/573; 250/577; 73/1.16; 73/861.47; 604/67; 702/49
(58) Field of Classification Search .................. 702/47, 702/50, 55, 100, 150, 49; 73/861, 32 R, 73/35, 1.16, 1.33, 451, 861.42, 861.47; 356/28; 250/573, 576, 577; 604/65, 67, 118
See application file for complete search history.

(56) References Cited

U.S. PATENT DOCUMENTS

| 4,090,514 A | 5/1978 | Hinck et al. |
| 4,191,184 A | 3/1980 | Carlisle |
| 4,470,758 A | 9/1984 | Pazemenas et al. |
| 4,539,005 A | 9/1985 | Greenblatt |
| 4,561,298 A | 12/1985 | Pond |
| 4,976,162 A | 12/1990 | Kamen |
| 5,207,645 A | 5/1993 | Ross et al. |
| 5,308,335 A | 5/1994 | Ross et al. |
| 5,348,539 A | 9/1994 | Herskowitz |
| 5,433,704 A | 7/1995 | Ross et al. |
| 5,464,391 A | 11/1995 | DeVale |

(Continued)

FOREIGN PATENT DOCUMENTS

WO    WO2007/098265 A2    8/2007

(Continued)

OTHER PUBLICATIONS

International Search Report and Written Opinion of the International Searching Authority dated Dec. 4, 2007, received in PCT/US2007/05095.

(Continued)

*Primary Examiner*—Kevin Pyo
(74) *Attorney, Agent, or Firm*—McLane, Graf, Raulerson & Middleton, Professional Association

(57) ABSTRACT

A fluid flow control system using flow rates to extract additional information from an in-line flow sensor. The system provides the ability to determine a position of a movable flow sensor element of a flow sensor by illuminating a photosensitive pixel array with a light source to create a first set of pixel intensity values introducing an abrupt change to the fluid driving pressure, illuminating the photosensitive pixel array with a light source to create a second set of pixel intensity values, and calculating the difference between the first and second sets of pixel intensity values as a function of pixel position.

18 Claims, 12 Drawing Sheets

U.S. PATENT DOCUMENTS

| | | |
|---|---|---|
| 5,533,381 A | 7/1996 | Seale |
| 5,554,123 A | 9/1996 | Herskowitz |
| 5,584,811 A | 12/1996 | Ross et al. |
| 5,597,042 A | 1/1997 | Tubel et al. |
| 5,624,409 A | 4/1997 | Seale |
| RE35,501 E | 5/1997 | Ross et al. |
| 5,743,878 A | 4/1998 | Ross et al. |
| 5,769,608 A | 6/1998 | Seale |
| 5,788,674 A | 8/1998 | McWilliams |
| 6,275,284 B1 | 8/2001 | Kiel et al. |
| 6,398,760 B1 | 6/2002 | Danby |
| 6,461,323 B2 | 10/2002 | Fowler et al. |
| 6,641,562 B1 | 11/2003 | Peterson |
| 6,642,999 B2 | 11/2003 | Arndt et al. |
| 6,685,668 B1 | 2/2004 | Cho et al. |
| 6,981,960 B2 | 5/2004 | Cho et al. |
| 7,503,903 B2 | 3/2009 | Carlisle et al. |
| 2005/0235733 A1 | 10/2005 | Holst et al. |
| 2010/0063765 A1* | 3/2010 | Carlisle et al. .............. 702/100 |

FOREIGN PATENT DOCUMENTS

| | | |
|---|---|---|
| WO | WO2007/098287 A2 | 8/2007 |
| WO | WO2007/106232 A2 | 9/2007 |

OTHER PUBLICATIONS

International Search Report and Written Opinion of the International Searching Authority dated Apr. 1, 2008, received in PCT/US2007/04945.

International Search Report and Written Opinion of the International Searching Authority dated Sep. 11, 2008, received in PCT/US2007/02039.

* cited by examiner

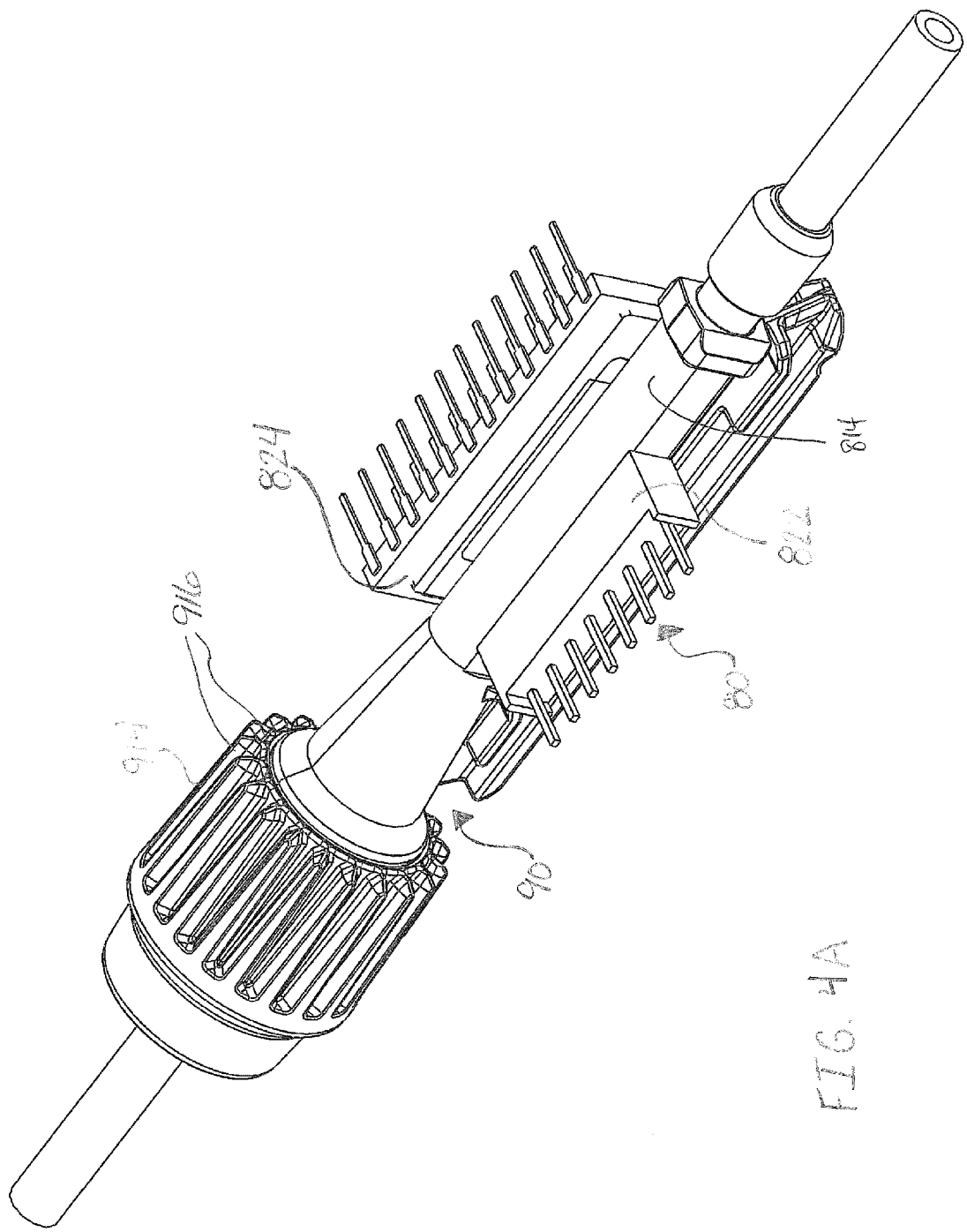

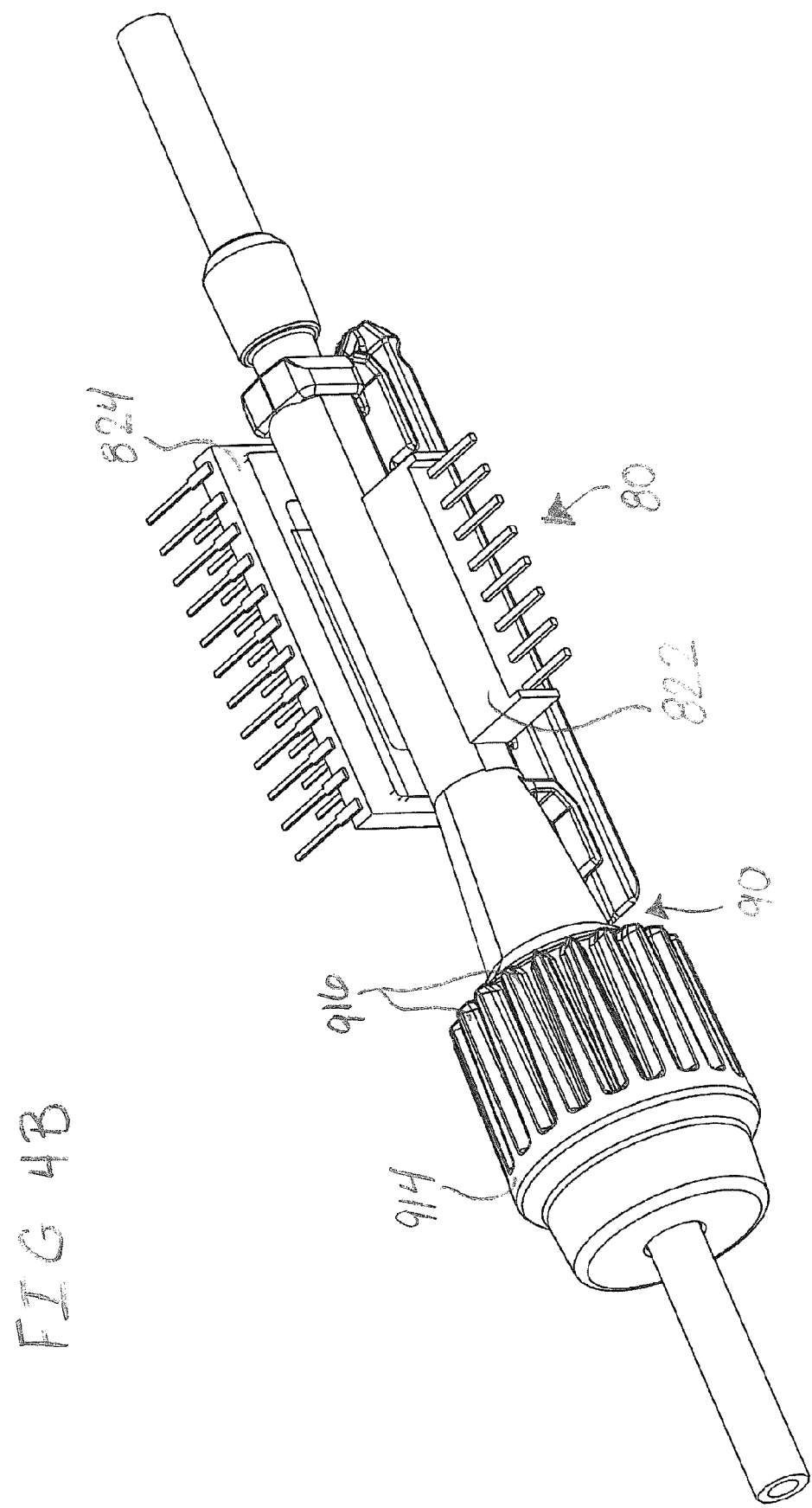

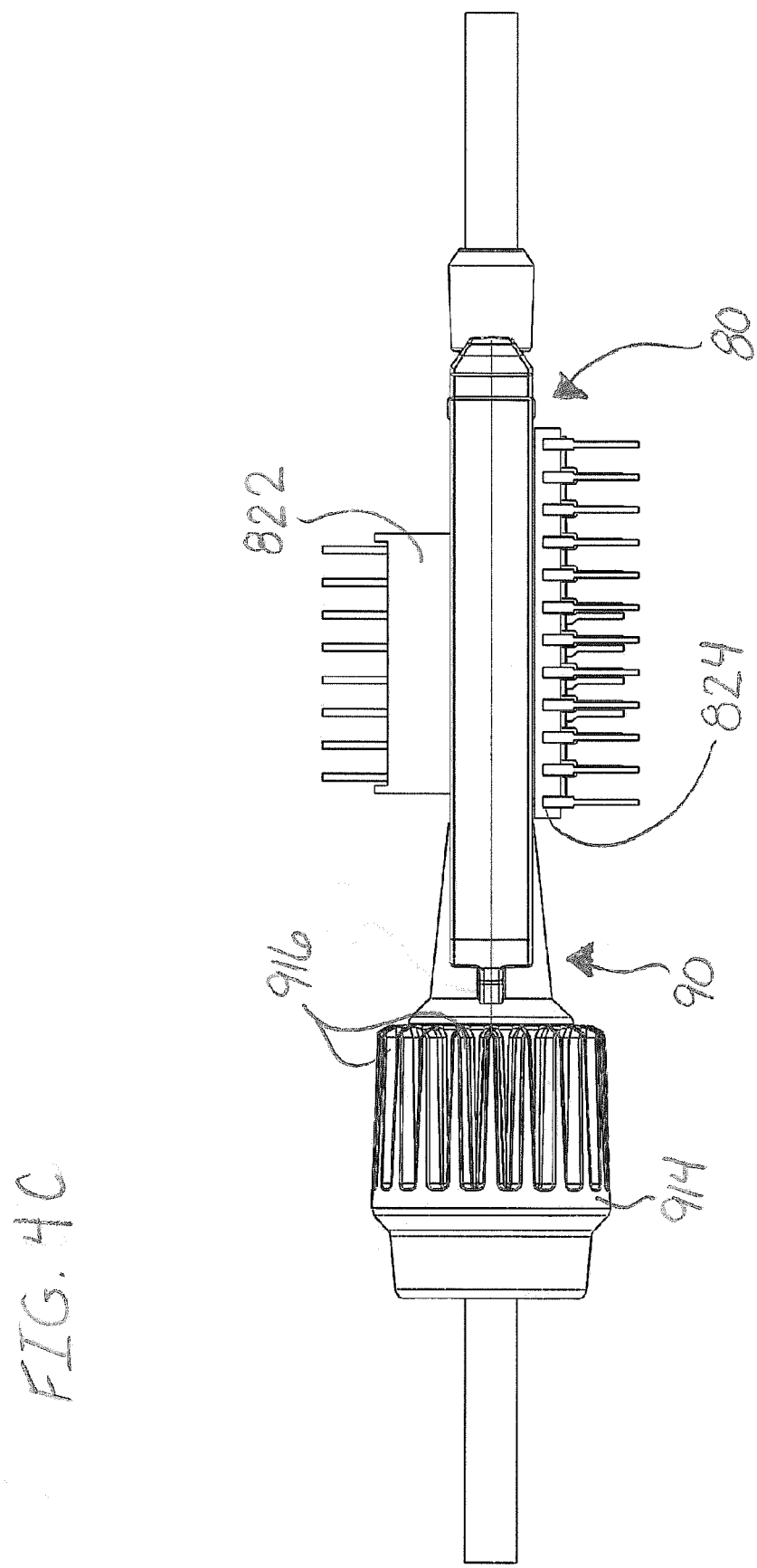

IMPULSE ANALYSIS FOR FLOW SENSOR-BASED FLUID CONTROL SYSTEM

BACKGROUND

The present disclosure relates to fluid flow control systems, such as intravenous infusion pumps, and more particularly to feedback control infusion pumps with flow sensing, volume sensing, variable pressure control, and variable flow resistance. In particular, the present disclosure relates to a method and apparatus for extracting enhanced information from an in-line fluid flow sensor by imposing an abrupt flow rate change.

A conventional large volume infusion pump is typically equipped with a motor that, in connection with a mechanical assembly and through the interface of a fluid barrier, pushes a small amount of fluid per motor "step." The mechanism might be a cam, a leadscrew, or other such assembly. The fluid barrier might be a syringe, an extruded tube, a molded cassette, or other such device that separates the pumping mechanism from the fluid in question. In each case, the fluid movement is determined by a certain number of motor steps over time.

At slow flow rates, the motor steps are relatively infrequent with long dwell periods. At high flow rates, the motor and mechanism are run at their maximal capacity until one element has reached its engineering limit. The flow rate is inherently pulsatile, yet this pulsatile nature is less significant at higher flow rates where the natural compliance of the outlet of the pumps serves to dampen the pulses into more or less a continuous stream of fluid.

The motors used conventionally are inherently powerful enough to overcome significant forces and resistances, so they are capable of generating significant pumping forces. This forceful pumping is an artifact and has no desirable clinical effect. The sensing mechanisms commonly used are pressure based and are made with indirect contact with the fluid to be pumped. In most cases, the fluid barrier, such as an extruded tube, exerts far more force than the internal fluid pressures. The result is a lack of sensitivity to pressure changes and a lack of feedback as to the actual conditions of fluid flow. It is common for conventional pumps to operate indefinitely without recognizing that the actual fluid flow rate is far below the targeted level.

Conventional motor driven pumps are notoriously inefficient with respect to external power consumption. For devices that have a high requirement for portability, this power inefficiency translates into unreliable operation.

Prior to the use of pumps, most infusions were done by the adjustment of a gravity-based pressure (e.g., by adjusting the height of a liquid container) and the adjustment of inline resistance (e.g., by moving the position of a roller clamp), both in response to an inline flow sensing method (e.g., performed by a user counting drops into an air chamber). Although this prior art method was labor intensive and had a limited rate range, it offered some significant advantages over the subsequent "advances" in technology. First, the use of gravity head heights for a delivery pressure was energy efficient. No external power supply was required. Second, the pressure was low, so the dangers of high-pressure infusions were avoided. Third, the gravity infusions could be augmented with a low cost and readily available pressure cuff, supplementing the fluid flow to rates well above those possible by an instrumented "pump" line. Forth, a gravity administration was not capable of infusing large amounts of air into the output line, because the hydrostatic pressure goes to zero as the fluid source empties.

An ideal infusion system will combine the meritorious aspects of a conventional "gravity" infusion with the benefits of a controlled intravenous infusion pump. In each aspect, this disclosure takes the desired principles of a gravity infusion and reduces the dependence upon skilled labor and extends the range and precision of fluid flow control and provides advanced information management capabilities.

An ideal embodiment of an infusion device would be one with continuous flow, wide flow rate range, high energy efficiency, accuracy of volume delivered over time, minimal operating pressures, maximum sensitivity to external conditions, freedom from false alarms for air-in-line, simplicity, low cost, intuitive operation, automated information exchange, safety, and reliability.

Certain infusions have historically been managed by air pressure delivery systems, most commonly found in the operating room and in emergency situations. Prior art attempts have been made to determine the flow rate via pressure monitoring and control. For example, U.S. Pat. No. 5,207,645 to Ross et al. discloses pressurizing an IV bag and monitoring pressure to infer flow rates. However, the prior art systems lack independent flow sensing, and, therefore, do not offer enough information to provide accurate and safe infusions.

Under the best of circumstances, there is not enough information in the pressure signal alone to provide the accuracy needed for intravenous infusion therapy. Furthermore, there are a number of likely failure modes that would go undetected using the pressure signal alone. An infusion pump must be able to respond to events in a relevant time frame. International standards suggest that a maximum period of 20 seconds can lapse before fluid delivery is considered "non-continuous." As an example, for an infusion of 10 ml/h, the system would want to resolve 20 seconds of flow, which corresponds to 0.056 mL. This volume represents one part in 18,000 of air volume of a 1,000 mL bladder. Temperature induced change in pressure brought about by a normal air conditioning cycle is far greater than this signal. The measurement of pressure alone is not adequate for an intravenous infusion device. No general purpose, full range, infusion devices using pressure-controlled delivery are known to be on the market.

An entire class of "passive" infusion pumps exists whereby a constant pressure is created on a fluid filled container by way of a spring, elastomeric structure, gas producing chemical equilibrium, or other means. This constant pressure fluid is fed into a high resistance output line, providing relatively stable fluid flow.

In typical pressure based flow control products, a relatively high pressure pushes fluid into a known, high, and fixed resistance, providing a constant flow rate with good immunity from changes in external conditions. It is a purpose of our prior commonly owned provisional application Ser. No. 60/777,193, filed on Feb. 27, 2006, and PCT Publication Nos. WO2007/098287, WO2007/098265, and WO2007/106232 to provide a highly flexible flow control system with a very broad flow rate range, operating under minimal pressures, with a relatively low and variable resistance. The entire contents of the aforementioned provisional and PCT applications are incorporated herein by reference.

Embodiments of such devices control fluid flow based on a responsive fluid flow sensing means that forms a closed loop control by changing both the fluid driving pressure and the inline resistance. In contrast to the conventional approach to flow control wherein a user observes fluid flowing as it formed drops in an air chamber, then adjusts pressure by varying the head height of the fluid source, and then adjusts the inline resistance via a manual valve, our above-mentioned disclosures employ a flow sensing apparatus and method that automatically and accurately measures fluid flow rate, precisely adjusts the hydrostatic pressure of the fluid source, and precisely adjusts inline fluid flow resistance to achieve or maintain a target flow rate.

SUMMARY

Certain embodiments of an in-line fluid flow sensor are based on the position of an object in the flow path in which the force of the fluid flow is balanced by an opposing force. The resultant equilibrium position is a function of the speed of fluid flow and of the fluid viscosity being measured.

The present disclosure describes an apparatus and method of enhancing the information derived from such an in-line fluid flow sensor by examining its response to an abrupt change in flow rate. The response of the fluid flow sensor can enhance the sensitivity of the measurement, may provide diagnostic value, and can provide additional information, such as fluid viscosity.

In certain embodiments of a fluid flow sensor, a signal can be analyzed to determine the position of an object in the flow path. This signal may have complex characteristics and the feature extraction that indicates the ball position may be challenged by the complexity of the signal. If a flow rate change is imposed upon the system, then the difference in the flow sensor signals taken at different flow rates will eliminate much of the underlying complexity and provide simplified feature extraction methods. In this way, the sensitivity of the flow sensor is enhanced, even with complex features or noisy environments.

At any given point in time, the flow sensor signal represents a certain flow rate. When a flow rate change is imposed by a change in fluid driving pressure, then the resultant response is an indication of total systemic fluid flow resistance. In an infusion control device, this measurement of fluid flow resistance can have significant clinical and diagnostic value.

In certain embodiments of a fluid flow sensor, the viscosity of the fluid will represent an offset in the position of a flow object. Taken by itself, however, the flow sensor may not be able to distinguish between a change in fluid viscosity and changes in flow sensor response due to normal manufacturing tolerances. If a flow rate change is abruptly applied, then the difference in flow sensor response in the sensor can be used to infer fluid viscosity, because the underlying offset due to manufacturing tolerances is eliminated from the analysis. The absolute change in flow object position as a function of flow rate change is an indication of fluid viscosity. In a further analysis, the speed with which the flow object moves to its new equilibrium position is an additional function of fluid viscosity and may be based on either or both of an absolute position change and rate of position change of the sensor object.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIGS. 4A and 4B are isometric views of an exemplary flow sensor with integral resistor showing the emitter and receiver.

FIG. 4C is a side view of the flow sensor embodiment appearing in FIGS. 4A and 4B.

DETAILED DESCRIPTION OF THE PREFERRED EMBODIMENTS

Figure 1:
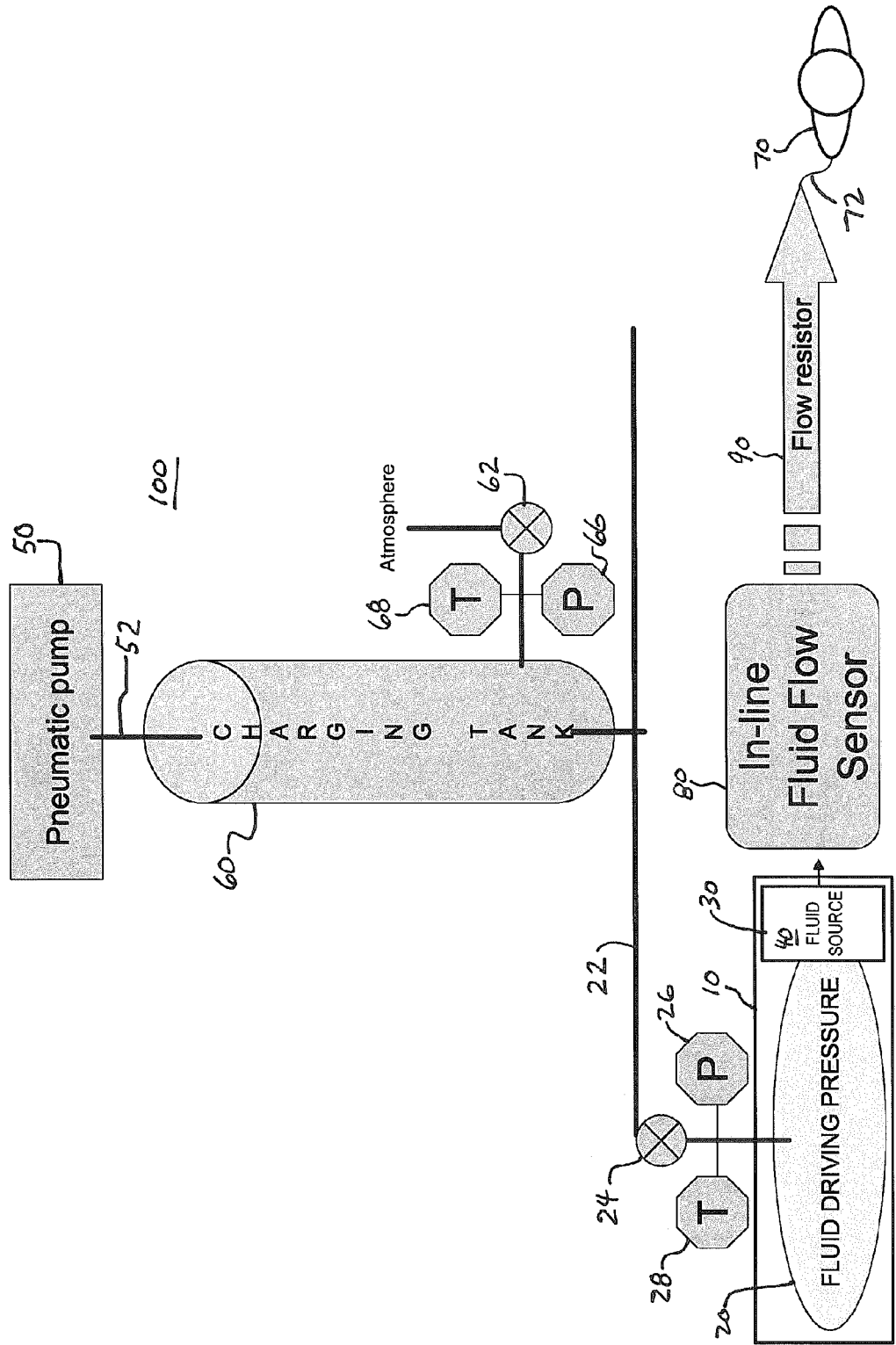
FIG. 1 is a functional block diagram of a fluid pumping system operable to embody an exemplary embodiment of the present invention.

Referring to the drawings, FIG. 1 depicts an exemplary flow control system 100 in accordance with an exemplary embodiment of the present invention. The system includes a pressure frame 10 that is of known total volume and contains within it an air bladder 20 and a flexible bag 30 that contains within it a liquid 40 to be delivered.

The air bladder 20 is connected to a charging tank 60 of known volume via a conduit or line 22 extending between an outlet of the tank 60 and an inlet of the bladder 20. A pneumatic pump 50 is pneumatically coupled to an inlet of the charging tank 60 via a line 52. A bladder valve 24 in the line 22 may be selectively opened and closed to selectively couple and decouple the outlet of the tank 60 with the inlet of the bladder 20. The charging tank may selectively be vented to atmosphere via a tank vent valve 62. The air bladder 20 may be vented to atmosphere via an optional bladder vent valve (not shown). Alternatively, the bladder 20 may be vented to atmosphere by opening the valves 24 and 62.

The tank 60 is connected to a tank pressure sensor 66 and a tank temperature sensor 68. The bladder 20 is connected to a bladder pressure sensor 26 and a bladder temperature sensor 28.

The liquid 40 is fluidically coupled to an output 70 via an inline flow sensor 80, a fluid flow resistor 90, and an output line 72. The liquid 40 may be, for example, a medication fluid, intravenous solution, blood product, or the like, to be infused and the output 70 may be, for example, a patient or subject in need thereof. In the depicted embodiment of FIG. 1, the flow resistor 90 is shown downstream of the in-line flow sensor 80. Alternatively, the flow resistor 90 may be positioned upstream of the flow sensor 80. The flow resistor 90 and flow sensor 80 may be separate or may be integrally formed.

Figure 2:
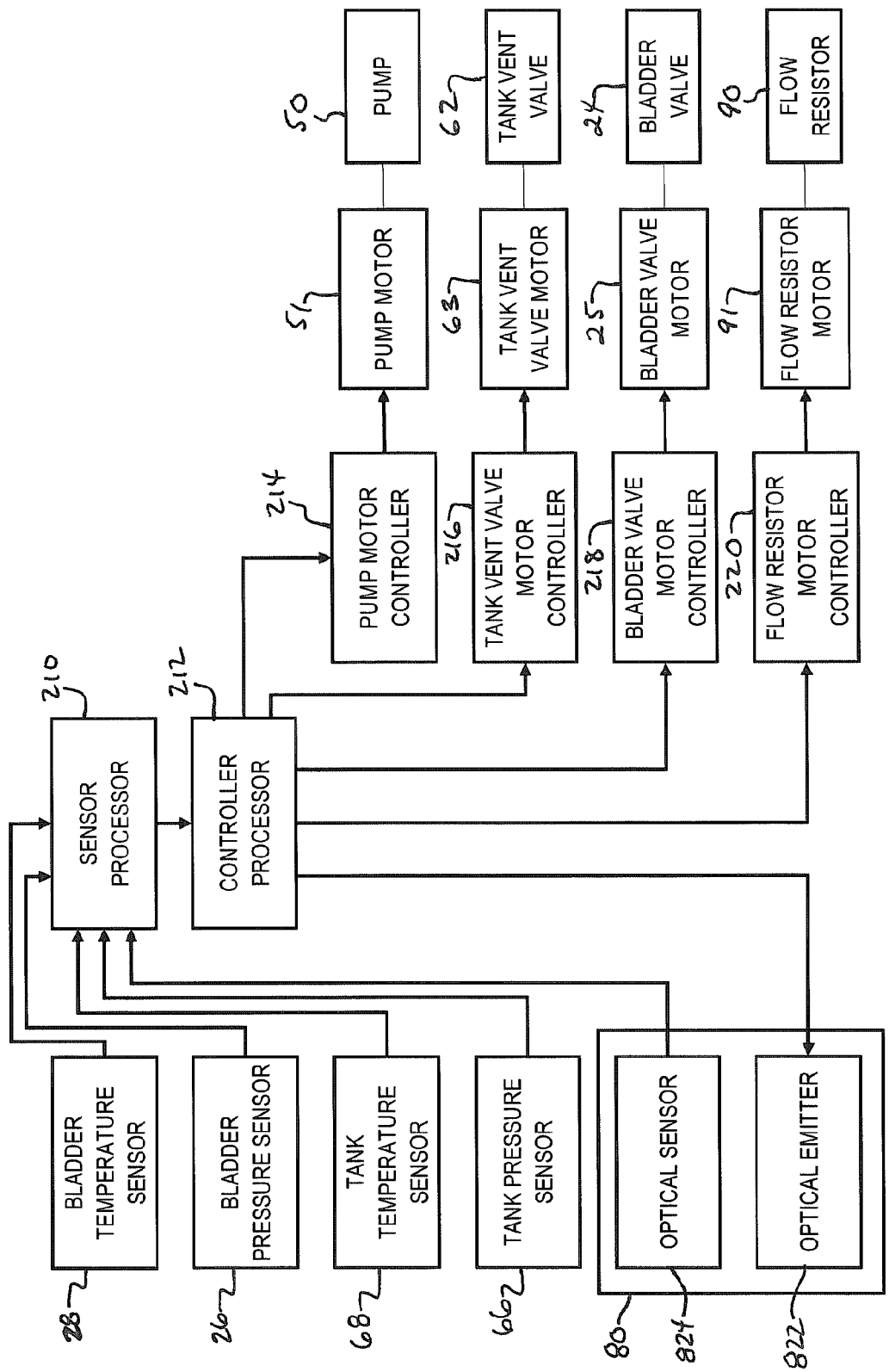
FIG. 2 is a functional block diagram flow sensor and control circuit for the system appearing in FIG. 1.

In reference to FIG. 2, an embodiment of the fluid control system 100 includes the pump 50 including a pump motor 51, the bladder valve 24 including a bladder valve motor 25, the tank vent valve 62 including a tank vent valve motor 63, the flow sensor 80 including an optical sensor 824 and an optical emitter 822, the flow resistor 90 including a flow resistor motor 91, the tank pressure sensor 66, tank temperature sensor 68, bladder pressure sensor 26, bladder temperature sensor 28, a sensor processor 210, a controller processor 212, a pump motor controller 214, a tank vent valve motor controller 216, a bladder valve motor controller 218 and a flow resistor motor controller 220.

The sensor processor 210, controller processor 212, pump motor controller 214, tank vent valve motor controller 216, bladder valve motor controller 218, and flow resistor motor controller 220 may be implemented in a microprocessor, microcontroller, controller, embedded controller, or the like. Although the processors 210 and 212 and the controllers 214-220 are depicted in FIG. 2 as discrete modules or processors for conceptual simplicity and ease of exposition, it is to be appreciated that modules 210-214 can share common hardware. Well-known internal components for processing and control modules, such as power supplies, analog-to-digital converters, clock circuitry, etc., are not shown in FIG. 2 for simplicity and would be understood by persons skilled in the art.

The controller processor 212 controls the pump 50 via the pump motor controller 214, the tank vent valve 62 via the tank vent valve controller 216, the bladder valve 24 via the bladder valve controller 218, and the flow resistor 90 via the flow resistor motor controller 220. Alternatively, the controller processor 212 may control one or more of the motors directly or via any other suitable known device. The controller 212 may also control the application of power to the optical emitter 822.

The sensor processor 210 receives a signal indicative of bladder temperature and pressure from the bladder temperature sensor 28 and bladder pressure sensor 26, respectively. The sensor processor 210 receives a signal indicative of tank temperature and pressure from the tank temperature sensor 68 and tank pressure sensor 66, respectively. The sensor processor 210 receives a signal from the optical sensor 824 indicative of the position of a flow sensor indicator element in the flow path as described below.

Figure 3:
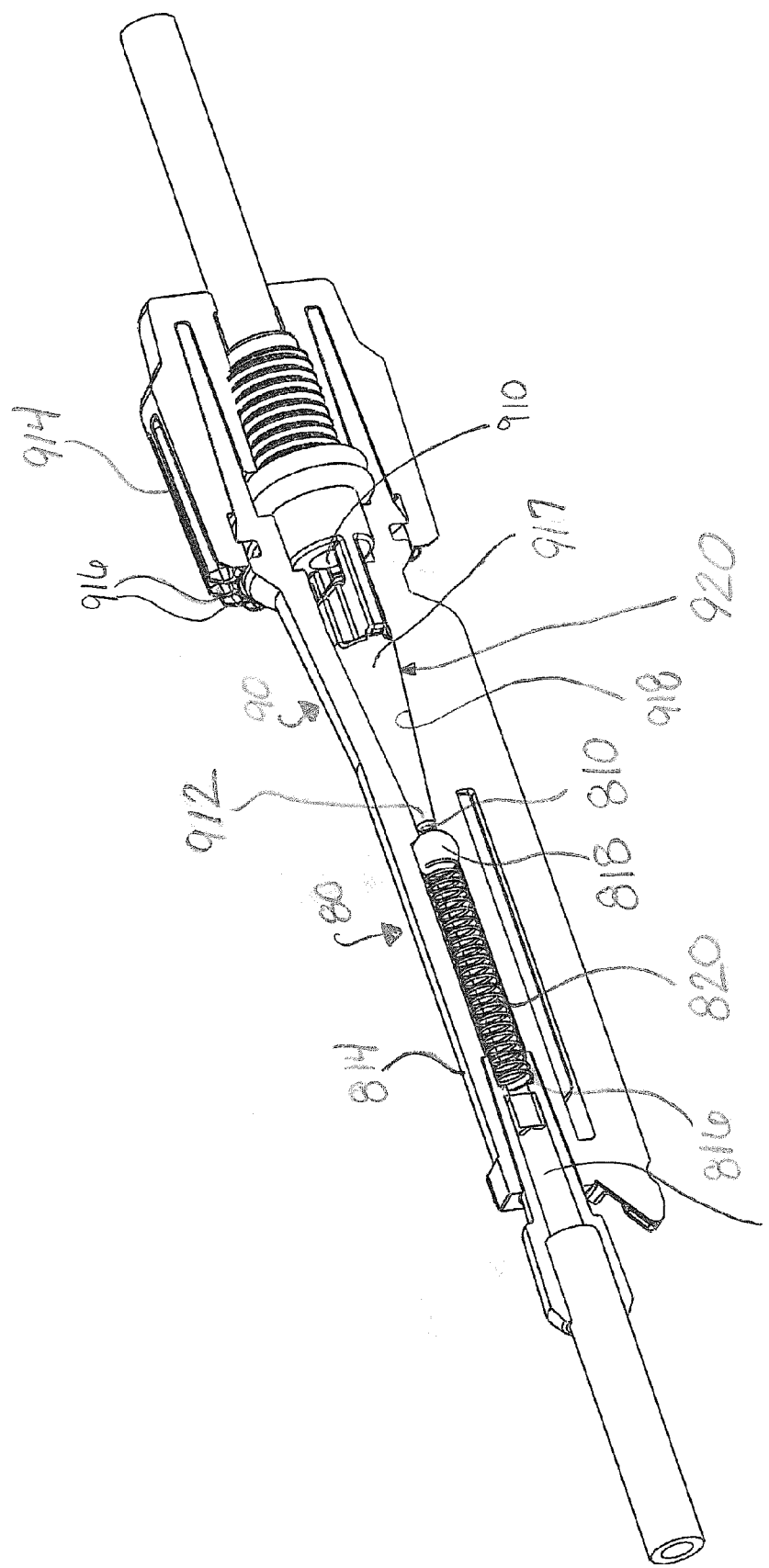
FIG. 3 is an isometric sectional view illustrating an exemplary flow sensor with integral resistor element.

FIG. 3 shows an exemplary flow sensor 80 with integral flow resistor 90. The flow resistor 90 includes an inlet end 910 fluidly coupled to the fluid source 40 and an outlet 912 fluidly coupled to an inlet 810 of the flow sensor 80. The flow sensor 80 includes an outlet end 812 fluidly coupled to the output 50 such as the vasculature of a patient, e.g., via an IV catheter or cannula as generally known in the art. Although the inline sensor 80 and flow restrictor 90 are depicted as an integral assembly in the embodiment of FIGS. 3 and 4A-4C, it will be recognized that the flow resistor and the flow sensor units may be discrete assemblies fluidically coupled in serial fashion.

In reference to FIGS. 3 and 4A-4C, the flow resistor 90 includes a rotatable housing 914, which may have a plurality of radially extending ribs or projections 916 forming a gear that may be selectively rotated by the motor 91, which may be a stepper motor having an intermeshing member, or the like. The rotatable housing 914 is coupled to an axially movable needle resistor 917 wherein rotating the housing 914 in one direction causes the needle resistor 917 to move in one axial direction and rotating the housing 914 in the opposite direction causes the needle resistor 917 to move in the opposite axial direction, for example, via helical threads formed on an interior surface of the rotatable housing member 914. As best seen in FIG. 3, the needle resistor axially moves between a first, closed position wherein the needle resistor engages a mating seat 918 and a fully open position. An annular gap 920 defined between the needle resistor 917 and the seat 918 increases as the valve moves from the closed position to the fully open position, thereby providing a variable flow resistance, which varies as a function of the degree of rotation of the housing 914.

The flow sensor 80 includes a housing portion 814 defining an axial channel or bore 816 receiving a ball member 818. A spring member 820 urges the ball member 818 in a direction opposite to the direction of flow. The spring member 820 may be a coil spring (e.g., conical or cylindrical coil spring) or may be another resiliently compressible material such as a foam member, deflectable band or leaf spring, or the like.

The spring 820 bears against the ball 818 and applies a force to the ball in the direction opposite to the direction of fluid flow. An adjustment mechanism, such as a threaded member engaging the fixed end of the spring 820 may be provided to axially advance or retract the fixed spring end to adjust the force preload of the spring 820 on the ball 818. In operation, fluid flow will exert a force on the sensor ball 818 against the urging of the spring 820, which force increases as the flow rate increases. The ball 818 thus moves until an equilibrium position is reached such that the force of the compression spring 820 on the ball 818 is balanced by the force of the fluid flow against the ball 818.

In reference to FIGS. 4A-4C, the optical emitter 822, which may be, for example, an LED array, is provided on a first side of the housing 814 and the optical receiver 824, which may be, a photosensitive array, charge-coupled device (CCD) array, photodiode array, complimentary metal oxide semiconductor (CMOS) digital detector array, or the like, is provided on a second side of the housing 814 opposite the first side. The optical emitter 822 transmits light through the housing 814 and into the cavity 816. The light incident upon the ball 818 is transmitted through the ball 818 and opposite wall of the housing 814 to form a light intensity pattern on the optical sensor 824. Where the fluid flowing through the channel 816 is a generally opaque fluid or otherwise has a high absorbance of the light emitted by the emitter 822, the ball 818 may be a clear ball, e.g., formed of acrylic or other transparent polymeric material, which serves to dramatically reduce the optical path length of the fluid in the optical path between the emitter 822 and the sensor 824 in the vicinity of the ball 818, thereby reducing the absorption of light by the fluid surrounding the ball in the flow passageway. Also, the use of a clear ball sensor element 818 allows the ball to function as a lens to transmit and focus the light.

The optical transmitter 822 may include one or more light source elements having a wavelength, for example, in the infrared (IR), visible, or ultraviolet (UV) region and the housing and ball member may be formed of a material that optically transmits light of the light source wavelength. The light source 822 may be an array of light elements, such as LEDs, or laser, etc. The light source may be segmented along the axis or may be a continuous, e.g., scanned or otherwise optically formed beam. The light source may illuminate the detector array along its length simultaneously or by sequentially scanning along its length. The refractive effect of a transparent ball member may have a focusing effect on the light passing therethrough that may be detected by the photosensor array. Alternatively, a nontransmissive ball 818 may be employed and the ball position may be determined by detecting the position of a shadow cast by the ball on the photosensor array. In still further embodiments, the ball member may have reflective surface and the optical sensor array may be positioned to detect light reflected from the surface of said ball.

The output from the photosensitive array is a set of pixel voltage values which vary in accordance with the amount of light impinging on the each pixel of the photosensitive array. The pixel voltage values may be sampled and digitized using an analog-to-digital converter and stored as digital data in an electronic storage medium as a numerical representation of the pixel output voltage levels, and thus, light intensity levels, along the detector array.

The output of the optical sensor 824 may be passed to the sensor processor 210, which may include a position-detection module or circuitry wherein the axial position of the ball 818 within the channel 816 is determined. The axial position of the ball 816 may in turn be used to determine a flow rate and/or calibrate or correlate ball positions with known flow rates calculated by other means such as plural volume measurements made using the method outlined in the aforementioned U.S. provisional application Ser. No. 60 and PCT Publication Nos. WO2007/098287, WO2007/098265, or WO2007/106232.

Figure 5:
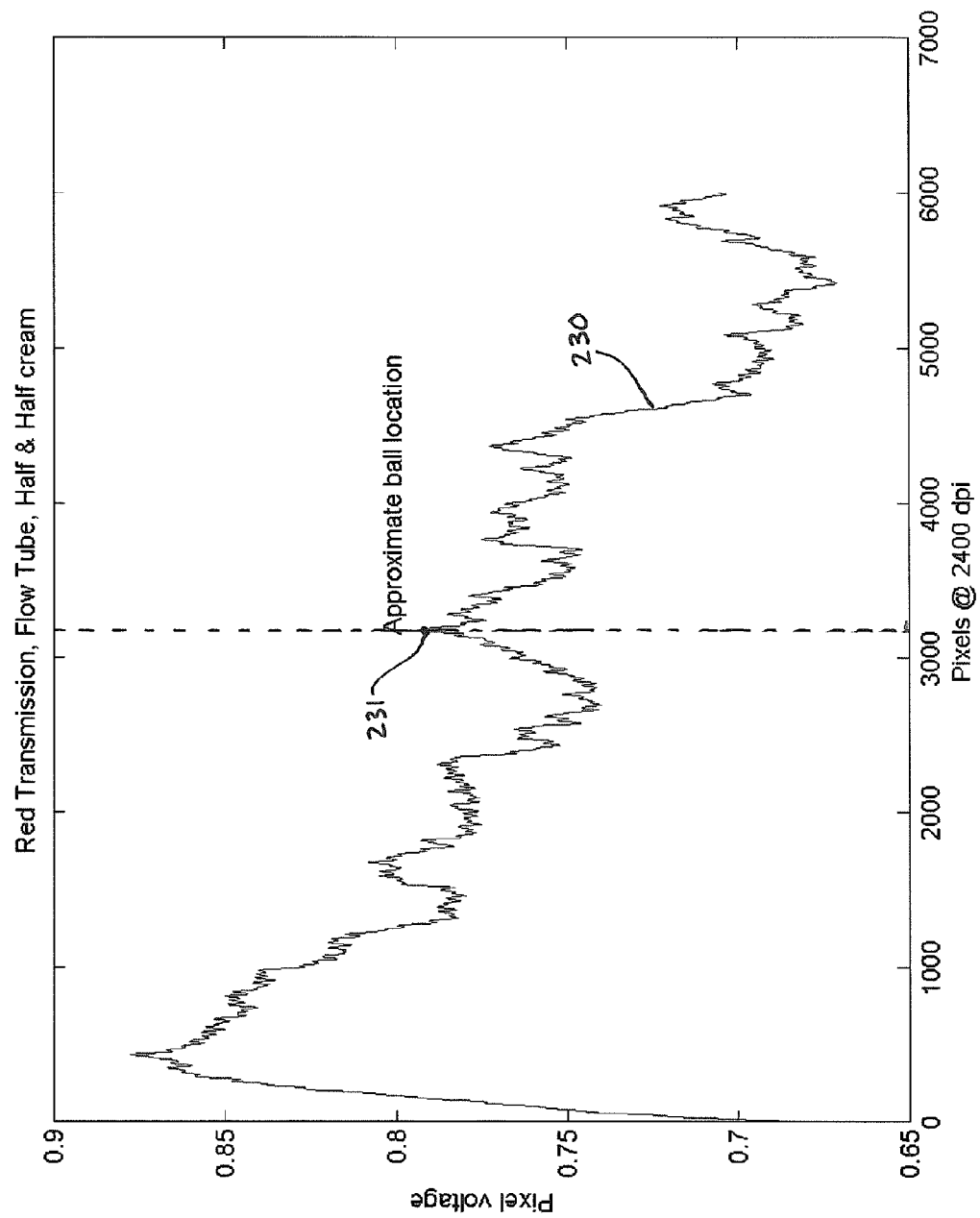
FIG. 5 is a graph of pixel voltage output for photosensor array for determining flow sensor element location.

Referring now to FIG. 5, there appears a graph of pixel voltage signal 230 of the photosensor array 824 as a function of pixel position. In the depicted example, the pixel voltage measurements were made using half-&-half as the fluid 40 and the flow sensor 80 was specifically detuned to represent a worst case scenario for the flow sensor and provide maximum challenge to the fluid control system. The graph of FIG. 5 shows that the flow sensor signal is complex and difficult to analyze for the position 231 of the flow object, which is somewhat ambiguous.

Figure 6:
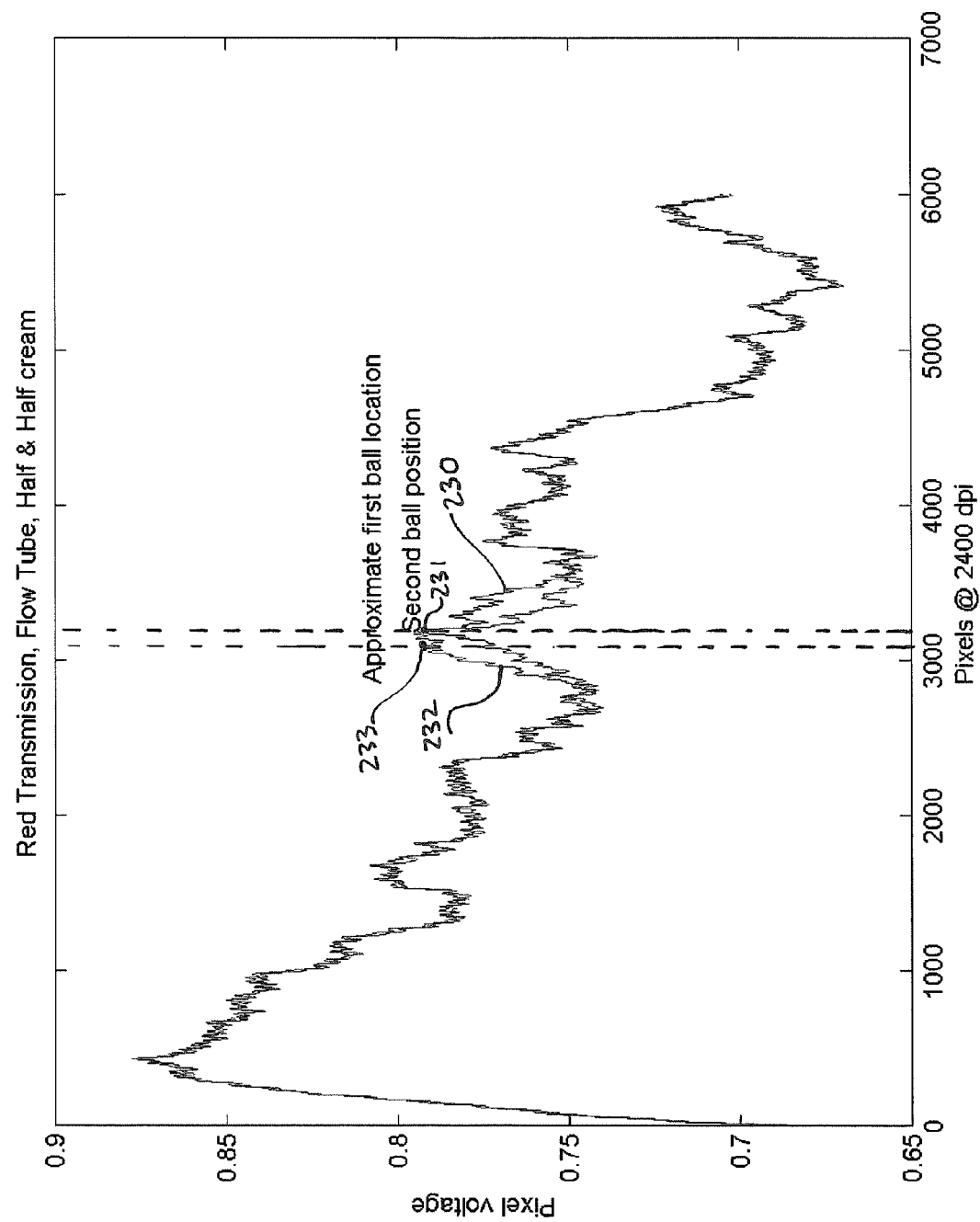
FIG. 6 is a graph of pixel voltage output for photosensor array with separate plots for flow sensor element location before and after a change in ball sensor element position.

Referring now to FIG. 6, the ball 820 was moved by the imposition of a modified flow rate and a subsequent measurement of the pixel voltage values of the photosensor array 824 was made (see signal 232). The new ball position 233, based on the pixel voltage values, is likewise somewhat ambiguous.

Figure 7:
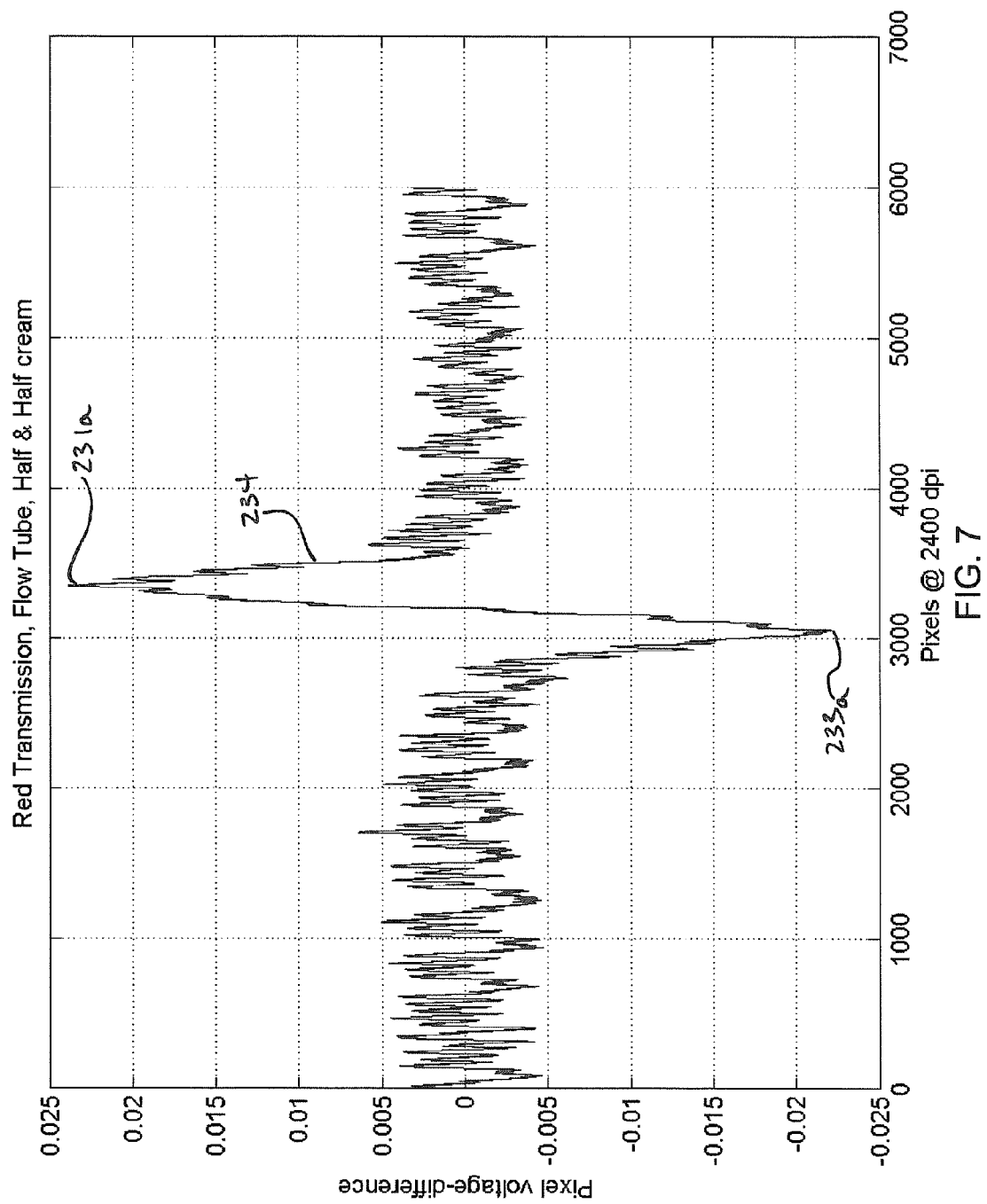
FIG. 7 is a graph of pixel voltage differences for the plots appearing in FIG. 6.

FIG. 7 is a graph 234 of the pixel voltage differences between the first signal 230 and the second signal 232. Subtracting the second signal from the first signal cancels or reduces common mode complexity and/or noise of the two signals and the first ball position 231a and second ball position 233a appear as clearly identifiable peaks, even though positions 231 and 233 based on the individual signals 230 and 232, respectively, were ambiguous. Alternatively, the first signal can be subtracted from the second signal, in which case the ball position can be similarly determined, but wherein the resultant function will be the negative function relative to the function 234 appearing in FIG. 7, i.e., reflected about the x-axis.

Figure 8:
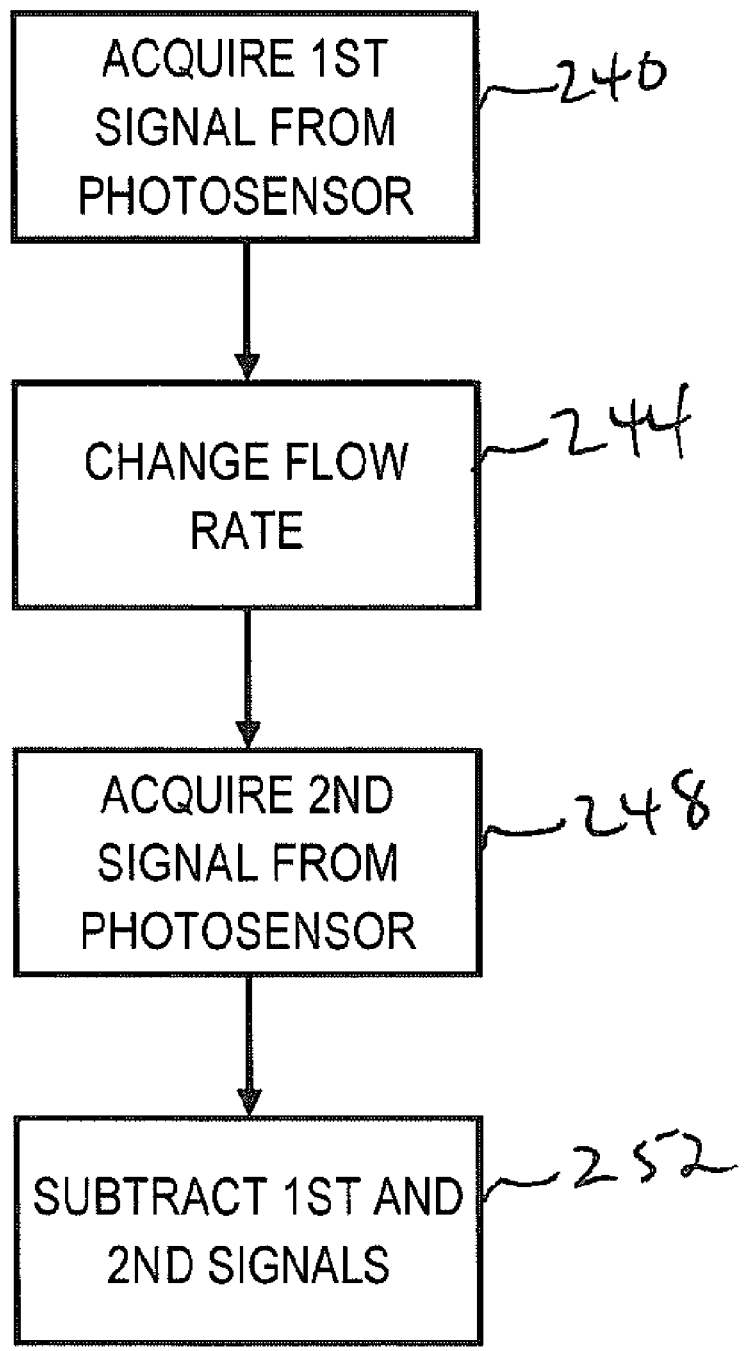
FIG. 8 is a flow diagram outlining an exemplary method for determining sensor element location in accordance with the present invention.

A method for detecting the flow sensor indicator element is outlined in the flowchart of FIG. 8. At step 240, a first signal from the photodetector array is provided to the sensor processor 210. At step 244, the flow rate is changed. The flow rate may be changed by introducing air into the charging tank 60 with the pump 50 to increase the pressure in the tank to a pressure greater than the pressure in the bladder 20 and opening the bladder valve 24. The pressure increase in the bladder 20 is preferably an abrupt pressure increase, e.g., to provide a step function change in fluid driving pressure, e.g., by popping or otherwise rapidly opening the valve 24. Alternatively, the change in flow rate may be a decrease in pressure. For example, if the pressure in the charging tank 60 is lower than the pressure in the bladder 20, then the rapid opening of the valve 24 will abruptly reduce the driving pressure. In alternative embodiments, an optional bladder vent valve (not shown) may be provided for venting the bladder to reduce the pressure in the bladder 20.

At step 248, a second signal from the photodetector array is provided to the sensor processor 210 representative of fluid flow rate at the new driving pressure. At step 252, one the first and second signals is subtracted from the other to provide clearly identifiable peaks representative of the ball axial position as described above.

It will be recognized that in a flow control system employing a pressurized bladder as the fluid driving force, it may be necessary to periodically increase the pressure in the bladder, for example, to achieve a desired flow rate. Also, once a desired flow rate has been achieved, periodic increases in the bladder 20 pressure will be necessary to maintain a desired flow rate since the bladder 20 will expand and the pressure in the bladder 20, and thus flow rate will thereby decay, as the fluid 40 exits the bag 30 and is delivered to the subject 70. Thus, even where the primary purpose of the pressure increase in the bladder 20 is to establish or maintain a desired flow rate, the observation of the ball position using the sensor 824 before and after the pressure increase in accordance with the present disclosure provides an additional benefit in that ball position can be determined with enhanced accuracy.

As discussed above, comparing ball position before and after an abrupt change in flow rate can advantageously be used to provide a clear indication of sensor ball position. In a further aspect, observation of ball position during the abrupt change in flow rate provides the ability to measure viscosity of the fluid 40. It has been found that viscosity of the fluid 40 can be determined by one or both of (1) the distance the ball moves in response to a change in flow rate (driving pressure); as well as (2) the rate at which the ball moves to the new position. The higher the viscosity, the further the ball moves in response to a change in flow rate. In addition, the higher the viscosity of the fluid, the longer it takes for the ball to assume its new equilibrium position in response to an abrupt change in flow rate.

Figure 9:
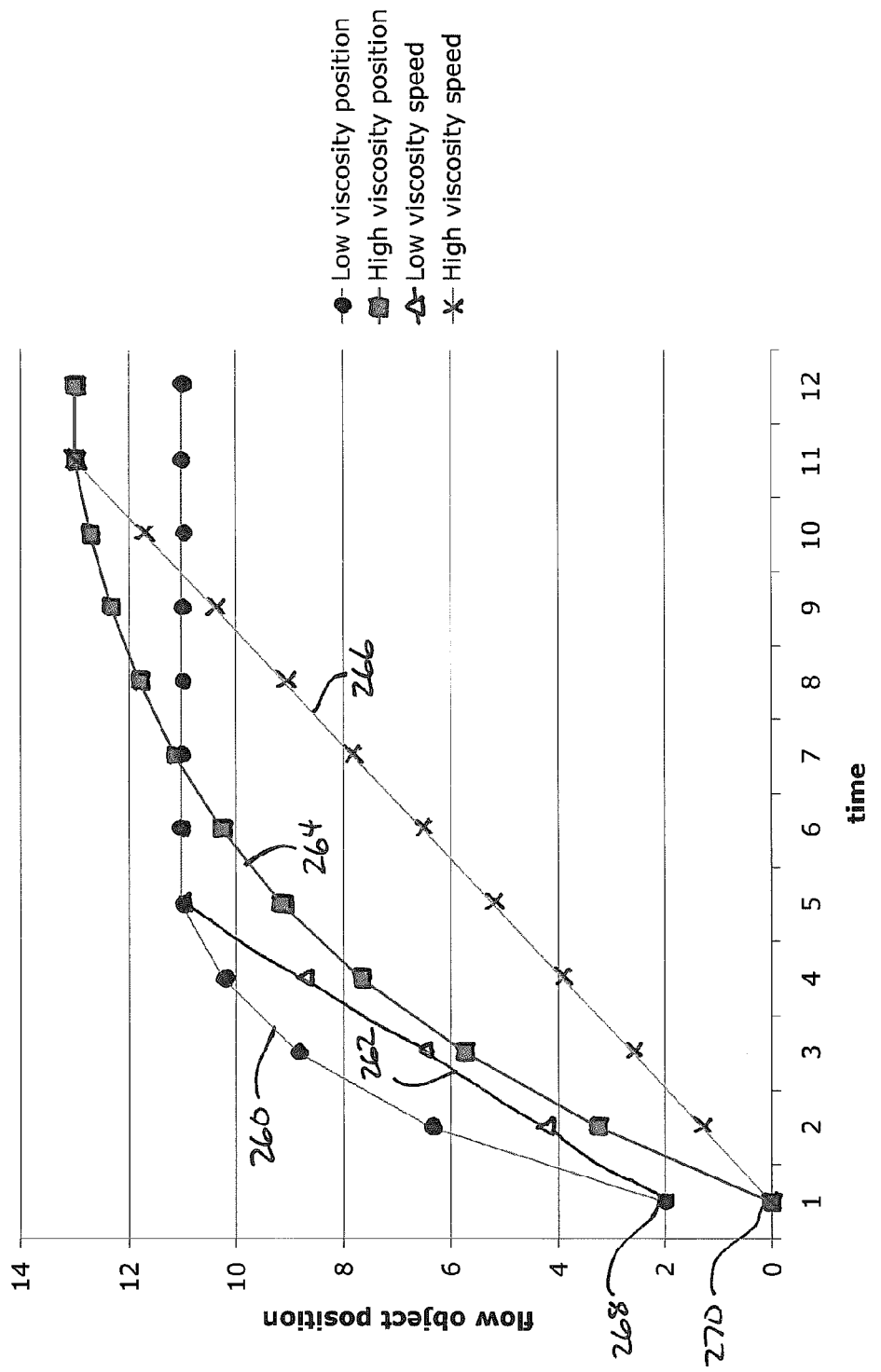
FIG. 9 is graph of flow sensor element position as a function of time during a period of an abrupt change in flow rate.

Referring now to FIG. 9, there appears a graph in which there is plotted a curve 260 representative of sensor ball position as a function of time during an abrupt increase in fluid driving pressure for a low viscosity fluid. The ball moved from position 2 to position 11, for a span of nine units of difference. The slope 262 represents the speed at which the sensor ball moved from its initial position to its final position for the low viscosity fluid. A curve 264 is representative of sensor ball position as a function of time for the same change in flow rate for a relatively high viscosity fluid. The ball moved from position 0 to position 13, for a span of 13 units of difference with the high viscosity fluid. The slope 266 represents the speed at which the sensor ball moved from its initial position to its final position for the high viscosity fluid.

The slope 266 for the high viscosity fluid is lower than the slope 262 for the low viscosity fluid, and the distance moved for the higher viscosity was greater than the distance moved for the lower viscosity fluid, thus indicating that, for higher viscosities, the fluid will push the ball further, yet will do so at a lower speed taking significantly longer to reach its equilibrium position. The graph also shows how the nominal starting positions 268 and 270 for the low and high viscosity fluids, respectively, for the same flow rates may vary due to the difference in viscosity.

Figure 10:
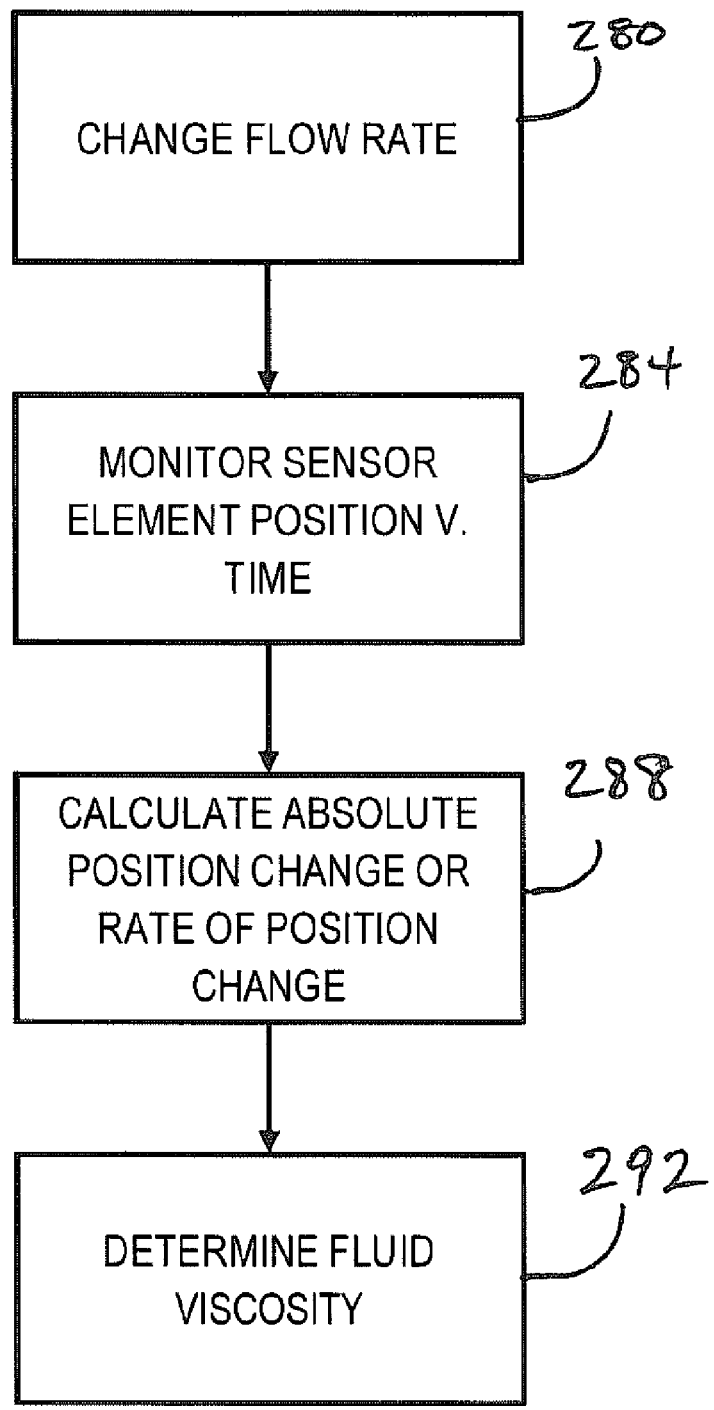
FIG. 10 is a flow diagram outlining an exemplary embodiment for sensing fluid viscosity in accordance with the present invention.

Referring now to FIG. 10, a method for determining the viscosity of a fluid being delivered in a flow control system is illustrated. At step 280, an abrupt change in flow rate is effected, e.g., by increasing the pressure in the tank 60 and popping the valve 24 to introduce a step change in fluid driving pressure. At step 284, the axial position of the sensor ball is monitored as a function of time during the flow rate change until the ball assumes a new equilibrium position. Alternatively, the change in flow rate may be effected by reducing the pressure in the bladder 20, e.g., by reducing the pressure in the tank 60 and popping the valve 24, or, by using an optional bladder vent valve (not shown).

At step 288, one or both of absolute position change and the rate of position change of the flow sensor element is calculated, e.g., by comparing ball pixel position along the sensor array and/or by determining the average slope of position as a function of time for the period of time in which it took the ball to move from its initial equilibrium position at the initial flow rate to its new equilibrium at the new flow rate. At step 292, the viscosity of the fluid being delivered is determined from the change in ball position and/or rate of sensor element response, for example, by comparing calculated ball position change and/or rate thereof to prestored values for fluids of known viscosity, which may be stored in database, look up table, data file, etc.

In operation, the type of fluid 40 to be infused may be input into the flow control system, e.g., by the operator using a user interface of the processor 210 and/or 212. Alternatively, the type of fluid 40 may be identified by reading a bar code (or other optically readable indicia) or radio frequency identification (RFID) tag on or in the fluid container, e.g., by a bar code (optical) scanner or RFID scanner. The viscosity as determined in step 292 may then be checked to determine whether it is consistent with an expected fluid viscosity based on prestored viscosity characteristics associated with the fluid type input by the operator (e.g., stored in a database, lookup table, data file, memory, etc.). For example, in the case of IV infusion fluids, many fluids or at least categories of fluids, such as blood products (e.g., whole blood, platelets, plasma, immunoglobulins, packed red cells etc.), saline, dextrose, albumin, lactated ringers solution, amino acids, lipid emulsions, parenteral nutritional solutions, etc., will have different viscosity characteristics. If the viscosity determined at step 292 is different from the expected viscosity, the operator may be alerted to this potential error condition, thereby providing an additional safeguard.

In further aspects, the observation of ball movement during an abrupt change fluid driving pressure may also be used to detect other error conditions. The change in flow rate in response to a change in fluid driving pressure is indicative of the total systemic resistance. For example, if the ball position does not change after the fluid driving pressure is increased, the line may be occluded, and the operator may be alerted to this potential error condition. Additionally, in the face of a potential occlusion, the pressure in the bladder may be reduced to a lower level, e.g., using a bladder vent valve, if provided, or by reducing the pressure in the charging tank 60 (e.g., via tank vent valve 62) and opening the bladder valve 24, e.g., to reduce the chance of an unwanted release bolus.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A method for determining a position of a movable flow sensor element of a flow sensor in a flow control system, the flow sensor being of a type having an axially-extending flow passageway for a liquid to be delivered by the flow control system, the movable sensor element being axially movable within the flow passageway in response to a first force exerted on the sensor element by the liquid as it passes through the flow passageway and in response to a second force exerted on the sensor element in a direction opposite the first force by a spring received within the flow passageway, the sensor reaching equilibrium position within the flow passageway when the magnitudes of the first and second forces are equal, the equilibrium position corresponding to a axial position within the flow passageway which varies with varying flow rate, the flow control system being of a type having a source of fluid driving pressure for driving the fluid through the flow passageway, the flow rate being responsive to variations in the fluid driving pressure, the method comprising:

illuminating a photosensitive pixel array with a light source, the photosensitive pixel array extending axially along the flow passageway and the sensor element disposed in an optical path between the light source and the photosensitive pixel array to generate a first set of pixel intensity values for the photosensitive pixel array, the first set of pixel intensity values representative of a first sensor element position corresponding to a first flow rate;

introducing an abrupt change in the fluid driving pressure;

illuminating the photosensitive pixel array with the light source to generate a second set of pixel intensity values for the photosensitive pixel array, the second set of pixel intensity values representative of a second sensor element position corresponding to a second flow rate;

calculating a difference between the first and second sets of pixel intensity values as a function of pixel position.

2. The method of claim 1, wherein the first and second sets of pixel intensity values are values representative of pixel voltages.

3. The method of claim 1, wherein the sensor element is an optically transmissive ball.

4. The method of claim 1, further comprising:

identifying a first pixel position corresponding to a maxima of the difference between the first and second sets of pixel intensity values and a second pixel position corresponding to a minima of the difference between the first and second sets of pixel intensity values, wherein the first pixel position is representative of one of the first sensor element position and the second sensor element position and the second position corresponds to the other of the first sensor element position and the second sensor element position.

5. The method of claim 4, further comprising:

using one or both of the first and second pixel positions to determine a rate of flow of the fluid in the flow control system.

6. The method of claim 4, further comprising:

calculating one or both of an axial distance between the first pixel position and the second pixel position and a rate of change of position of the sensor element between the first sensor element position and the second sensor element position.

7. The method of claim 6, further comprising:

correlating one or both of said axial distance between the first pixel position and the second pixel position and said rate of change of position of the sensor element between the first sensor element position and the second sensor element position with a viscosity.

8. The method of claim 7, wherein said correlating is performed by comparing one or both of said axial distance between the first pixel position and the second pixel position and said rate of change of position of the sensor element between the first sensor element position and the second sensor element position with known sensor element behavior for one or more fluids of known viscosity, said known sensor element behavior associated with said known viscosity.

9. The method of claim 7, further comprising:

inputting fluid identifying information;

determining an expected viscosity based on said fluid identifying information;

comparing said viscosity determined by said correlating with said expected viscosity;

if said viscosity is not within some predetermined threshold of said expected viscosity, outputting an indication of an error condition.

10. The method of claim 1, wherein the abrupt change in the fluid driving pressure is an abrupt increase in the fluid driving pressure.

11. An optical position measurement apparatus for determining a position of a movable flow sensor element of a flow sensor in a flow control system, the flow sensor being of a type having an axially-extending flow passageway for a liquid to be delivered by the flow control system, the movable sensor element being axially movable within the flow passageway in response to a first force exerted on the sensor element by the liquid as it passes through the flow passageway and in response to a second force exerted on the sensor element in a direction opposite the first force by a spring received within the flow passageway, the sensor reaching equilibrium position within the flow passageway when the magnitudes of the first and second forces are equal, the equilibrium position corresponding to a axial position within the flow passageway which varies with varying flow rate, the flow control system being of a type having a source of fluid driving pressure for driving the fluid through the flow passageway, the flow rate being responsive to variations in the fluid driving pressure, the apparatus comprising:
- a light source and a photosensitive pixel array for illumination with said light source, the photosensitive pixel array extending axially along the flow passageway and the sensor element disposed in an optical path between the light source and the photosensitive pixel array;
- a processor receiving signals from said photosensitive pixel array to generate a first set of pixel intensity values for the photosensitive pixel array, the first set of pixel intensity values representative of a first sensor element position corresponding to a first flow rate and a second set of pixel intensity values for the photosensitive pixel array, the second set of pixel intensity values representative of a second sensor element position corresponding to a second flow rate;
- a source of pressurized air for introducing an abrupt change in the fluid driving pressure;
- said processor calculating a difference between the first and second sets of pixel intensity values as a function of pixel position.

12. The apparatus of claim 11, wherein the first and second sets of pixel intensity values are values representative of pixel voltages.

13. The apparatus of claim 11, wherein the sensor element is an optically transmissive ball.

14. The apparatus of claim 11, further comprising:
- said processor identifying a first pixel position corresponding to a maxima of the difference between the first and second sets of pixel intensity values and a second pixel position corresponding to a minima of the difference between the first and second sets of pixel intensity values, wherein the first pixel position is representative of one of the first sensor element position and the second sensor element position and the second position corresponds to the other of the first sensor element position and the second sensor element position.

15. The apparatus of claim 14, further comprising:
- said processor using one or both of the first and second pixel positions to determine a rate of flow of the fluid in the flow control system.

16. The apparatus of claim 14, further comprising:
- said processor calculating one or both of an axial distance between the first pixel position and the second pixel position and a rate of change of position of the sensor element between the first sensor element position and the second sensor element position.

17. The apparatus of claim 16, further comprising:
- a database storing known sensor element behavior for one or more fluids of known viscosity and correlating said known sensor element behavior with viscosity.

18. The apparatus of claim 16, further comprising:
- said processor determining viscosity by comparing one or both of said axial distance between the first pixel position and the second pixel position and said rate of change of position of the sensor element between the first sensor element position and the second sensor element position with said known sensor element behavior.

* * * * *